United States Patent
Aubry et al.

(10) Patent No.: US 7,101,337 B2
(45) Date of Patent: Sep. 5, 2006

(54) METHOD AND NON-INVASIVE DEVICE FOR FOCUSING ACOUSTIC WAVES

(75) Inventors: Jean-Francois Aubry, Bourg la Reine (FR); Mathias A. Fink, Meudon (FR); Mickaël Tanter, Paris (FR); Jean-Louis Thomas, Villejuif (FR)

(73) Assignee: Centre National de la Rechercher Scientifique - CNRS, Paris (FR)

( * ) Notice: Subject to any disclaimer, the term of this patent is extended or adjusted under 35 U.S.C. 154(b) by 465 days.

(21) Appl. No.: 10/399,634

(22) PCT Filed: Oct. 17, 2001

(86) PCT No.: PCT/FR01/03208

§ 371 (c)(1),
(2), (4) Date: Sep. 4, 2003

(87) PCT Pub. No.: WO02/32316

PCT Pub. Date: Apr. 25, 2002

(65) Prior Publication Data

US 2004/0054282 A1   Mar. 18, 2004

(30) Foreign Application Priority Data

Oct. 20, 2000   (FR) .................................. 00 13501

(51) Int. Cl.
*A61B 8/15*   (2006.01)

(52) U.S. Cl. ........................... 600/447; 73/602; 73/626

(58) Field of Classification Search ................ 600/437, 600/443, 447; 73/602, 625–6
See application file for complete search history.

(56) References Cited

U.S. PATENT DOCUMENTS

| 3,934,458 | A  |   | 1/1976  | Beretsky et al. |
|-----------|----|---|---------|-----------------|
| 5,207,214 | A  |   | 5/1993  | Romano |
| 5,268,876 | A  | * | 12/1993 | Rachlin ......................... 367/7 |
| 5,531,117 | A  | * | 7/1996  | Fortes .......................... 73/602 |
| 5,566,675 | A  | * | 10/1996 | Li et al. ...................... 600/459 |
| 5,581,517 | A  | * | 12/1996 | Gee et al. .................... 367/138 |
| 5,675,554 | A  |   | 10/1997 | Cole et al. |
| 6,198,829 | B1 | * | 3/2001  | Fink et al. ............... 381/71.12 |
| 6,485,423 | B1 | * | 11/2002 | Angelsen et al. ........... 600/458 |
| 6,490,469 | B1 | * | 12/2002 | Candy ........................ 600/407 |

(Continued)

OTHER PUBLICATIONS

International Search Report for Application No. PCT/FR01/03208; report dated Jun. 25, 2001.

(Continued)

*Primary Examiner*—Francis J. Jaworski
(74) *Attorney, Agent, or Firm*—Marshall, Gerstein & Borun LLP

(57) ABSTRACT

The invention concerns a method for focusing acoustic waves useful for obtaining an image of a field to be observed in a dissipative heterogeneous medium (2, 3) around which acoustic transducers (T1–Tn, T'1–T'm) forming an imaging network and a target network. The method consists in following a training step during which pulse responses from the medium are measured between each transducer (Ti) of the imaging network (5) and several transducers (Tj) of the target network (6); deducing therefrom reference signals to be emitted by the transducers of the imaging network to produce a focused acoustic pulse in each transducer of the target network, then cumulatively, in determining reference signals to be emitted to focus an acoustic pulse on predetermined points in the medium. Said reference signals are stored and used subsequently to generate an acoustic image of the medium.

23 Claims, 1 Drawing Sheet

U.S. PATENT DOCUMENTS 6,699,189 B1 * 3/2004 Lin et al. .................... 600/437
6,705,993 B1 * 3/2004 Ebbini et al. ............... 600/443

OTHER PUBLICATIONS

French Search Report for French Application No. FR 0013501; report dated Jul. 12, 2001.

T.F. Hueter, "The Detection of Intracranial Tumors by Use of Ultrasound," *Q. Prog. Rep. Acoustics Laboratory*, Massachusetts Institute of Technology, Cambridge MA, Jan.-Mar. pp. 23-24 (1951).

D.N. White et al., "The Deformation of Ultrasound Field in Passage Across the Living and Cadaver Head," *Med. Biol. Engng.*, vol. 7, pp. 607-618 (1969).

F.J. Fry et al., "Transkull Visualization of Brain Using Ultrasound: an Experimental Study," *Ultrasound in Medicine*, Excerpta Medica, Amsterdam, pp. 97-101 (1974).

DJ Philips, et al., "A phase compensation technique for B-Mode echoencephalography," *Ultrasound in Medicine*, Plenum New York, vol. 1, pp. 345-404 (1975).

J.L. Thomas et al., "Ultrasound Beam Focusing Through Tissue Inhomogeneities with a Time Reversal Mirror; Application to Transkull Therapy," *IEEE Trans. Ultrasound, Ferroelec. Freq. Contr.* vol. 43 N° 6. pp. 1122-1129 (1996).

M. Tanter, et al., "Focusing and Steering Through Absorbing and Aberrating Layers: Application to Ultrasound Propagation Through the Skull," *Journal of Acoustical Society of America*, 103 (5) pp. 2403-2410 May (1998).

M. Tanter, et al., "Time Reversal and the Inverse Filter," *Acoustical Society of America*, Jun. (2000).

J. Ytalo et al. "Ultrasound Echo Tomography Through Skulbone," *Ultrasound Symosium*, pp. 1019-1022 (1989).

M. Tanter, et al., "Focusing Through Skull with Time Reversal Mirrors Application to hyperthermia," *IEEE Ultrasonics Symposium Proceedings*, San Antonio, USA Nov. (1996).

M. Tanter, et al., "Comparison Between Time Reversal Focusing in Absorbing Medium and Inverse Filtering," *IEEE Ultrasound Symposium Proceedings* Toronto, Canada, vol. 2, pp. 1741-1745 Oct. (1997).

M. Tanter, et al. "Focalisation à travers le crâne par retournement temporal. Application à l'hyperthermie," *Actes du 4ème Congrè Français d'Acoustique*, vol. 1, pp. 149-153, Marseille (1997).

M. Tanter, et al., "Ultrasound focusing and steering through skull: Towards brain imaging," *The Journal of the Acoustic Society of America*, Seattle, USA Jun. 1998-135th Meeting: Seattle, Washington (ICA/ASA '98) Jun. 1998.

Mallart et al., "The Van Cittert Zernicke Theorem in Pulse-echo Measurement," *J. Acoustic Soc., Am* 90(5), Nov. 1991).

Mallart et al., "Adaptative Focusing in Scattering Media Through Sound Speed in Homogeneities: The van Cittert Zernicke Approach and Focusing criterion," *J. Acoustic Soc. Am.*, vol. 96, No. 6, pp. 3721-3732 Dec. (1994).

Fink, "Time Reversed Acoustics," *Scientific America* pp. 67-73 Nov. (1999).

Fink, "Les Miroirs à retournement temporal," (time reversal mirrors) *Pour La Science* N° 268 Février (2000).

* cited by examiner

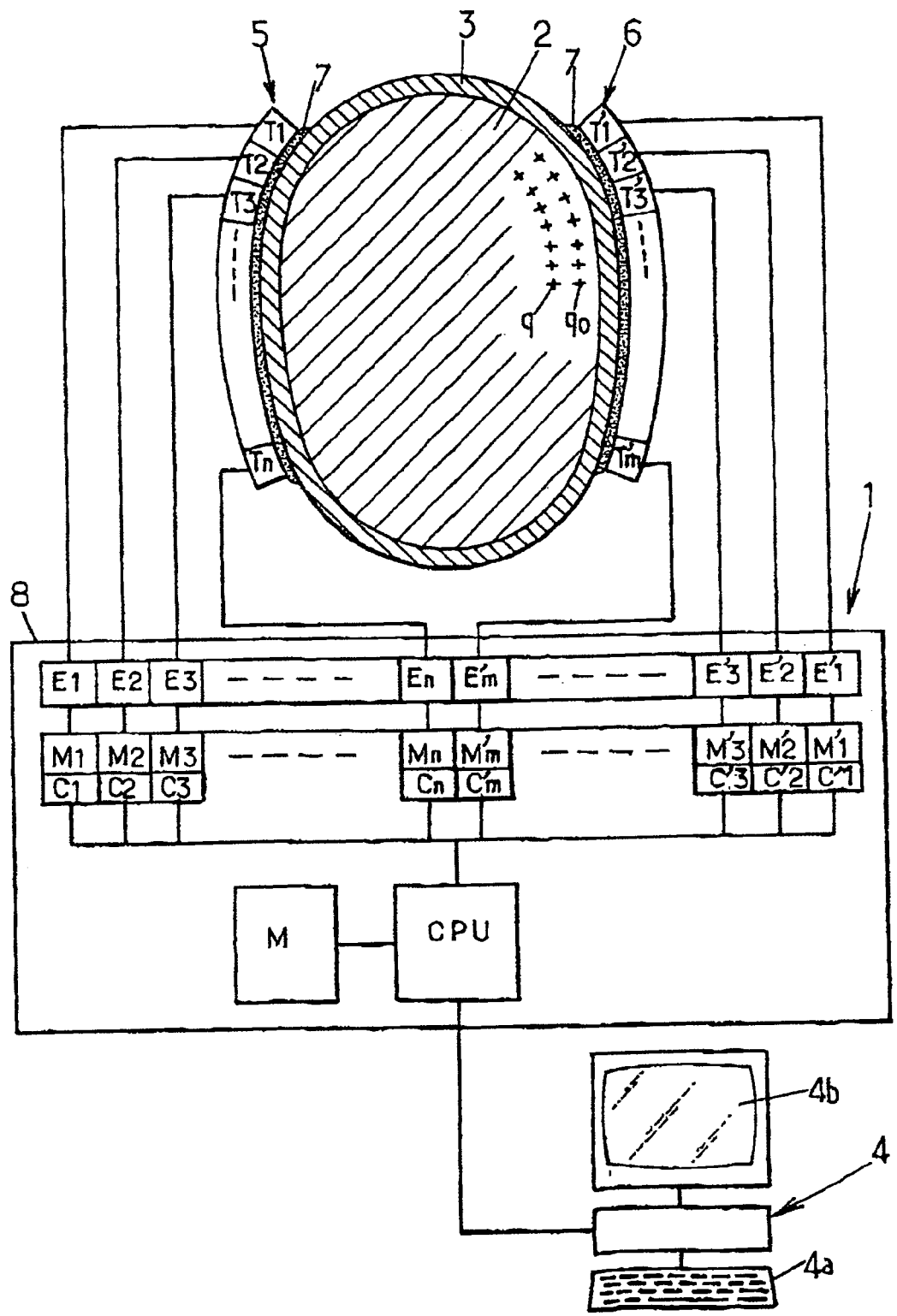

METHOD AND NON-INVASIVE DEVICE FOR FOCUSING ACOUSTIC WAVES

FIELD OF THE DISCLOSURE

This application is a 371 of PCT/FR01/03208 filed on Oct. 17, 2001.

The present invention relates to noninvasive methods and devices for focusing acoustic waves, in particular ultrasound waves.

BACKGROUND OF THE DISCLOSURE

More particularly, the invention relates to a noninvasive method for focusing acoustic waves in a dissipative heterogeneous medium comprising a substantially homogeneous medium (for example the brain) surrounded at least partially by a dissipative aberrating layer (for example the skull) which generates aberrations in the propagation of the acoustic waves, the acoustic waves being emitted from outside the aberrating layer and focused in the substantially homogeneous medium.

The methods of this type which are commonly used do not make it possible to obtain good focusing of the acoustic waves inside the medium, and, when these methods are used in imaging applications, they therefore do not make it possible to obtain a good resolution and a good image contrast when the propagation aberrations are significant, for example when echography of the brain is being carried out from outside the skull.

It is, in particular, an object of the present invention to overcome this drawback.

SUMMARY OF THE DISCLOSURE

To this end, according to the invention, a focusing method of the type in question is characterized in that it includes the following steps:

(a) an initial positioning step during which a number t greater than 2 of acoustic transducers are fixed in predetermined positions outside the aberrating layer, these transducers being in (direct or indirect) contact with said aberrating layer and forming at least:

an imaging array which combines a number n between 1 and t of said transducers, and a target array which combines a number m between 1 and t of said transducers (these two arrays may be entirely separate, or include certain common transducers, or alternatively each include all of the aforementioned transducers), (b) a learning step itself comprising the following substeps:

(b1) a substep of learning to focus the imaging array on the target array, during which substep:

(b11) impulse responses hri(t) of the dissipative heterogeneous medium are determined, respectively between each transducer i of the imaging array and a plurality of focusing points r lying on the aberrating layer in respective correspondence with transducers of the target array (this determination may be carried out by direct measurement if the transducers of the target array are made to emit acoustic pulses, or optionally by measurement and calculation if the transducers of the target array are made to emit acoustic signals other than pulses; the values measured and/or calculated in this way may then optionally be corrected by digital backpropagation in order to simulate transducers lying directly in contact with the aberrating layer if the transducers are not in direct contact with the aberrating layer), these impulse responses being stored in digital form with a certain time sampling which determines a number p of frequency components of the impulse response, with respective frequencies $\omega k$, i being an index between 1 and n which designates a transducer of the imaging array, r being an index between 1 and m which designates a focusing point corresponding to a transducer of the target array and k being an index between 1 and p which designates a frequency component, (b12) on the basis of these impulse responses, for each focusing point r corresponding to a transducer of the target array, a set of n reference time signals e'i(t,r) is calculated, i varying between 1 and n, such that if the aberrating wall were removed in the vicinity of the focusing point r, the emission of these reference signals by the various transducers i of the imaging array would generate a predetermined signal (for example an acoustic pulse) focused on the focusing point r, (b2) a substep of focusing at a number R of predetermined focusing points lying in the substantially homogeneous medium, with indices q between m+1 and m+R, this substep consisting in determining for each of these focusing points q, moving step-by-step away from the focusing points 1 to m corresponding to the transducers of the target array, reference signals e'i(t,q) to be emitted by the various transducers i of the imaging array in order to generate a pulse focused on said focusing point q, the reference signals e'i(t,q) being determined for each focusing point q by proceeding as follows:

(b21) a first estimate of e'i(t,q), for i ranging from 1 to n, is calculated on the basis of at least one reference signal e'i(t,q0), q0 being the index of at least one focusing point close to the focusing point q for which the reference signal has already been determined, this calculation being performed by using an average speed of the acoustic waves in the substantially homogeneous medium (2), (b22) the transducers of the imaging array are made to emit, by iterations, the estimates previously obtained of the reference signals e'i(t,q), then signals $s_i(t,q)$ back-scattered by the dissipative heterogeneous medium are picked up with the same transducers, then these reference signals e'i(t,q) are modified for the next iteration in the following way:

$$e_i'(t) \to \alpha_i(q).e_i'(t-\tau_i(q))$$

where the values $\alpha_i(q)$ and $\tau_i(q)$ are a corrective amplitude factor and a corrective delay, which are calculated so as to maximize a coherence criterion C between said back-scattered signals, said iterations being stopped when the criterion C reaches a predetermined threshold, (b3) the reference signals e'i(t,q) are stored, at least for q between m+1 and m+R, (c) and a focusing step during which, for at least one of said focusing points q, the transducers of the imaging array are made to emit said reference signals e'i(t,q), i being an index between 1 and n designating a transducer of the imaging array.

By virtue of these provisions, the propagation aberrations of the acoustic waves in the dissipative heterogeneous medium are overcome and very precise focusing is obtained, which may in particular make it possible to obtain reliable and precise echography of a field to be observed through the aberrating layer by back-scattering, when acoustic waves focused on different points of the field to be observed are successively emitted and the back-scattered acoustic waves are picked up.

This precise focusing may also be used in applications other than echography, in particular:
Doppler color imaging,
elastographic imaging methods, such as the one described in document WO-A-00/55 616,
nonlinear imaging methods ("harmonic imaging"),
methods of treatment by localized destruction of a part of the dissipative heterogeneous medium, in particular by hyperthermia,
methods for measuring optical absorption parameters of tissues with activation by ultrasound, etc.

In preferred embodiments of the invention, one and/or other of the following provisions may optionally be implemented:

during substep (b11), when at least certain transducers (of the target array and/or the imaging array) are in contact with an intermediate homogeneous medium (for example a gel) which is itself in contact with the aberrating layer, the impulse responses hri(t) are corrected by digital backpropagation in order to simulate transducers lying directly in contact with the aberrating layer;

substep (b12) itself includes the following substeps:

(b121) p transfer matrices H(ωk)=[Hri(ωk)] are determined, i ranging from 1 to n and r ranging from 1 to m, where Hri(ωk) is the value, at the frequency ωk, of the Fourier transform of the impulse response hri(t), (b122) for each focusing point r corresponding to a transducer of the target array, n components Ei(ωk,r) are determined, i varying between 1 and n, such that F(ωk,r)= H(ωk).E(ωk,r), where E(ωk,r)=[Ei(ωk,r)] is a vector with n components, F(ωk,r) is a vector with m components Fl(ωk,r), l varying between 1 and m, these m components Fl(ωk,r) corresponding to a desired focusing of the acoustic waves at the frequency ωk on the focusing point r corresponding to a transducer of the target array, (b123) for each focusing point r corresponding to a transducer of the target array, a vector of n time signals e(t,r)=[ei(t,r)] is deduced therefrom, i varying between 1 and n, where $$e_i(t, r) = \sum_{k=1}^{P} Ei(\omega k, r) \cdot e^{j\omega k, t}$$

in complex notation, these signals ei(t,r) being adapted so that the emission of them respectively by the various transducers i of the imaging array generates an acoustic pulse focused on the focusing point r of the target array, (b124) a substep of correcting the aberrations generated by the aberrating layer between the substantially homogeneous medium and each target transducer r, these aberrations being estimated on the basis of the measurements carried out previously, the aberrations estimated in this way being used to calculate said reference time signals e'i(t,r);

p matrices $H^{-1}(\omega k)$ are calculated during substep (b122), respectively by regularization and inversion of the transfer matrices H(ωk), and the vector E(ωk,r) is calculated for each transducer r of the target array by the formula:

$E(\omega k, r) = H^{-1}(\omega k).F(\omega k, j)$;

during step (b122), the components Fl(ωk,r) of the vector F(ωk,r) corresponding to the spatial distribution of the desired field at the frequency ωk are equal to 0 for l≠r and to 1 for l=r;

during substep (b124), the aberrating wall in the vicinity of each focusing point r corresponding to a transducer of the target array is assimilated to a filter, which has a finite impulse response and is defined at each frequency ωk by an amplitude Gr(ωk) and a phase $\phi_r(\omega k)$, substep (b124) itself including the following substeps:

(b1241) for each frequency ωk, the amplitude Gr(ωk) and the phase $\phi_r(\omega k)$ are calculated on the basis either of the signals ei(t,r) or of the vectors E(ωk,r), (b1242) p corrected transfer matrices H'(ωk)=[H'ji(ωk)] are calculated, where $$H'_{ji}(\omega_k) = H_{ji}(\omega_k) \cdot \frac{1}{G_j(\omega_k)} e^{-j\phi_j(\omega_k)},$$

(b1243) for each transducer r of the target array, n components E'i(ωk,r) are determined, i varying between 1 and n, such that F(ωk,r)=H'(ωk).E'(ωk,r), where E'(ωk,r)= [Ei(ωk,r)] is a vector with n components, F(ωk,r) is a vector with m components Fl(ωk,r), l varying between 1 and m, these m components Fl(ωk,r) corresponding to a desired focusing of the acoustic waves at the frequency ωk on the focusing point r corresponding to a transducer of the target array, (b1244) for each focusing point r corresponding to a transducer of the target array, a vector of n reference time signals e'(t,r)=[e'i(t,r)] is deduced therefrom, i varying between 1 and n, where $$e'_i(t, r) = \sum_{k=1}^{n} E'i(\omega k, r) \cdot e^{j\omega k, t}$$

in complex notation;

during substep (b2141), the amplitude Gr(ωk) and the phase $\phi_r(\omega k)$ are calculated as follows:

$$Gr(\omega_k) = \frac{\sqrt{\sum_{i=1}^{n} E_i(\omega_k, r0) \cdot E_i^*(\omega_k, r0)}}{\sqrt{\sum_{i=1}^{n} E_i(\omega_k, r) \cdot E_i^*(\omega_k, r)}}$$

$$\phi_r(\omega_k) = \frac{1}{n}\sum_{i=1}^{n} (\arg(E_i(\omega_k, r0)) - \arg(E_i(\omega_k, r)e^{-j\Delta\tau(r0,r,i)\omega_k}))$$

where:
Ei* is the complex conjugate value of Ei,
and Δτ(r0,r,i)=(d(r0,i)−d(r,i))/c, d(r,i) being the distance between the transducer i and the focusing point r, and d(r0,i) being the distance between the transducer i and a particular focusing point r0;

substep (b12) itself includes the following substeps:

(b121) p transfer matrices H(ωk)=[Hri(ωk)] are determined, i ranging from 1 to n and r ranging from 1 to m, where Hri(ωk) is the value, at the frequency ωk, of the Fourier transform of the impulse response hri(t), (b122') the transfer matrices H(ωk) are corrected in order to overcome the aberrations generated by the aberrating wall in the vicinity of each focusing point r, this correction being carried out on the basis of the impulse responses hri(t)

determined previously, and corrected transfer matrices H'(ωk) are obtained in this way, (b123') for each focusing point r corresponding to a transducer of the target array, n components E'i(ωk,r) are determined, i varying between 1 and n, such that F(ωk,r)= H'(ωk).E'(ωk,r), where E'(ωk,r)=[E'i(ωk,r)] is a vector with n components, F(ωk,r) is a vector with m components Fl(ωk,r), l varying between 1 and m, these m components Fl(ωk,r) corresponding to a desired focusing of the acoustic waves at the frequency ωk on the focusing point r corresponding to a transducer of the target array, (b124') for each focusing point r corresponding to a transducer of the target array, a vector of n time signals e'(t,r)=[e'i(t,r)] is deduced therefrom, i varying between 1 and n, where $$e'_i(t,r) = \sum_{k=1}^{P} E'i(\omega k, r) \cdot e^{j\omega k \cdot t}$$

in complex notation, the signals e'i(t,r) being said reference signals;

p matrices $H'^{-1}(\omega k)$ are calculated during substep (b123'), respectively by regularization and inversion of the transfer matrices H'(ωk), and the vector E'(ωk,r) is calculated for each transducer r of the target array by the formula:

$$E'(\omega k,r)=H'^{-1}(\omega k).F(\omega k,j);$$

during step (b123'), the components Fl(ωk,r) of the vector (ωk,r) corresponding to the spatial distribution of the desired field at the frequency ωk are equal to 0 for l≠r and to 1 for l=r;

during substep (b122'), the aberrating wall in the vicinity of each focusing point r corresponding to a transducer of the target array is assimilated to a filter, which has a finite impulse response and is defined at each frequency ωk by an amplitude Gr(ωk) and a phase $\phi_r(\omega k)$, substep (b122') itself including the following substeps:

(b122'1) for each frequency ωk, the amplitude Gr(ωk) and the phase $\phi_r(\omega k)$ are calculated on the basis of the impulse responses determined previously, (b122'2) p corrected transfer matrices H'(ωk)=[H'ji(ωk)] are calculated, where $$H'_{ji}(\omega k) = H_{ji}(\omega_k) \cdot \frac{1}{G_j(\omega k)} e^{-j\phi_j(\omega_k)};$$

during substep (b122'1), the amplitude Gr(ωk) and the phase $\phi_r(\omega k)$ are calculated for each frequency ωk in the following way:

$$Gr(\omega_k) = \frac{\sqrt{\sum_{i=1}^{n} H_{ri}(\omega_k) \cdot H_{ri}^*(\omega_k)}}{\sqrt{\sum_{i=1}^{n} H_{r0,i}(\omega_k) \cdot H_{r0,i}^*(\omega_k)}}$$

$$\phi_r(\omega_k) = \frac{1}{n}\sum_{i=1}^{n} (\arg(H_{ri}(\omega_k)e^{j\Delta\tau(i,r,r0)\omega k}) - \arg(H_{r0,i}(\omega_k))), \text{ where:}$$

H*ri designates the complex conjugate value of Hri, and Δτ(r0,r,i)=(d(r0,i)−d(r,i))/c, d(r,i) being the distance between the transducer i and the focusing point r, and d(r0,i) being the distance between the transducer i and a particular focusing point r0;

during step (c), substep (c1) is followed by the following substeps:

(c2) said transducers of the imaging array are made to pick up signals $s_i(t)$ back-scattered by the dissipative heterogeneous medium, (c3) the reference signal emitted by each transducer of the imaging array is convoluted with the back-scattered signal picked up by this transducer, (c4) then the convolution products obtained in this way are summed, step (c) being repeated for a plurality of points lying in the substantially homogeneous medium;

during substep (b21), the first estimate of each reference signal is e'i(t,q)=e'i(ts+θi(q),q0) for each focusing point q, q0 being the index of a focusing point close to the focusing point q for which the reference signal has already been determined, θi(q) being a delay equal to a value δi(q)/c, where c is the average speed of the acoustic waves in the medium, and δi(q) is equal to a difference between, on the one hand, a distance between the transducer i of the imaging array and the focusing point q0, and, on the other hand, a distance between the transducer i of the imaging array and the focusing point q;

during substep (b2), when at least certain transducers with index v of the imaging array are not directly in contact with the aberrating layer, the corresponding signals $e'_v(t,q)$ are corrected by digital backpropagation in order to simulate transducers placed in direct contact with the aberrating layer;

during substep (b22), the values $\alpha_i(q)$ and $\tau_i(q)$ are looked for to maximize the following coherence criterion C:

$$C = \frac{<\left|\sum_{i=1}^{n} \alpha_i \cdot g_i(t - \tau_i, q)\right|^2>}{n \cdot \sum_{i=1}^{n} <\left|\alpha_i \cdot g_i(t - \tau_i, q)\right|^2>}, \text{ where:}$$

$g_i(t,q)=s_i(t)\otimes e_i(t,q)$, $\hat{x}$ representing the convolution operation, and <> represents a time average;

during substep (b22), the values $\tau_i(q)$ are calculated by maximizing a cross-correlation function, for transducers close to the imaging array, of the signals $g_i(t,q)$ and $g_{i+1}(t,q)$;

during substep (b22), the values $\alpha_i(q)$ are calculated so as to equalize the maximum amplitude of the functions $g_i(t,q)$ on the index i;

during substep (b22), the values $\alpha_i(q)$ and $\tau_i(q)$ are calculated by carrying out a cross-correlation, for transducers close to the imaging array, of the signals $g_i(t,q)$ and $g_{i+1}(t,q)$;

during substep (b22), the values $\alpha_i(q)$ and $\tau_i(q)$ are calculated so as to equalize the maximum amplitude of the functions $g_i(t,q)$ on the index i;

substep (b22) relating to each focusing point q is carried out immediately after substep (b21) relating to the same focusing point q;

the dissipative heterogeneous medium consists of the brain surrounded by the skull;

the imaging array and the target array are two separate arrays arranged on either side of the dissipative heterogeneous medium;

all the transducers belong both to the imaging array and to the target array;

the acoustic waves are ultrasound waves.

The invention furthermore relates to a device designed for implementing the method defined above.

Other characteristics and advantages of the invention will become apparent during the following description of one of its embodiments, which is given by way of nonlimiting example with reference to the appended drawing.

BRIEF DESCRIPTION OF THE DRAWINGS

In the drawing, the single FIGURE represents an ultrasound imaging device according to one embodiment of the invention.

DETAILED DESCRIPTION OF THE DISCLOSURE

The ultrasound imaging device 1 represented in the drawing is designed to produce an ultrasound echographic image of a patient's brain 2 (at frequencies of, for example, the order of from 1 to 3 MHz) from outside the skull 3, the brain 2 constituting a substantially homogeneous medium for propagation of the acoustic waves and the skull 3 constituting a dissipative aberrating layer, so that the overall cranium 2, 3 constitutes a dissipative heterogeneous medium.

As a variant, the invention could be applicable, in particular:

to acoustic imaging of any other nonhomogeneous dissipative heterogeneous medium comprising a substantially homogeneous medium surrounded by a relatively thin dissipative layer generating aberrations in the propagation of the ultrasound waves, or to any other method involving at least one focusing upon emission into such a medium.

In the example represented in the drawing, the imaging device 1 includes a microcomputer 4, or any other device for control and/or visualization of ultrasound images, this microcomputer conventionally including a keyboard 4a, optionally combined with other control interfaces, and a screen 4b making it possible to visualize the images of the brain 2.

The imaging device 1 furthermore includes two arrays 5, 6 of ultrasound transducers T1, T2 ... Tn and T'1, T'2 ... T'm forming, for example, two linear banks of transducers which are arranged on either side of the user's skull 3, in predetermined geometrical positions with respect to one another, each transducer bank 5, 6 being brought into contact with the skull 3 via a layer 7 of gel or the like.

The various transducers T1, T2 ... Tn and T'1, T'2 ... T'm may be controlled directly by the microcomputer 4, or preferably by a central electronic unit CPU which is contained, for example, in an electronics rack 8 and is itself controlled by the microcomputer 4.

Advantageously, each of the transducers T1, T2 ... Tn, T'1, T'2, T'm is connected to a sampler, respectively E1, E2 ... En, E'1, E'2, E'm, and each sampler is itself connected to a memory, respectively M1, M2 ... Mm, M'1, M'2 ... M'm and to a central unit C1, C2 ... Cm, C'2, C'2 ... C'm. These memories and these central units are in turn connected, directly or indirectly, to the aforementioned central unit CPU, which is furthermore connected to at least one central memory M.

The device which has just been described operates as follows.

Initially, the two arrays of transducers 5, 6 are fixed on either side of the patient's skull 3, in said predetermined positions. To this end, the arrays of transducers 5, 6, respectively referred to as the imaging array and the target array, may be carried by a rigid support such as a hat (not shown) arranged around the patient's head.

The device then follows a learning step lasting a few minutes (advantageously from 1 to 3 min), making it possible to take account of all the propagation aberrations due to the nonhomogeneous nature of the dissipative medium formed by the skull 3 and the brain 2.

During this learning step, firstly each of the transducers T1, T2 ... Ti, ... Tn, of the imaging array 5 is made to successively emit an acoustic pulse, and, for each pulse emitted by one of the transducers Ti of the imaging array, the signal picked up by the transducers T'1, T'1 ... T'r, ... T'm of the target array 6 is recorded, that is to say the impulse response hri(t) of the dissipative heterogeneous medium between the transducer i in question of the imaging array 5 and each transducer j of the target array 6.

Each impulse response hri(t) is recorded in digital form with a certain time sampling which determines a certain number p of monochromatic frequency components of the impulse response, each corresponding to a frequency $\omega k$, k being an index between 1 and p.

In the case envisaged here, where at least certain transducers of the target array and/or of the imaging array are not directly in contact with said aberrating layer 3, the impulse responses are corrected in order to simulate virtual transducers arranged in contact with said aberrating layer. The position of the layer with respect to the transducers may optionally be obtained by conventional imaging (ultrasound echography, x-ray scanner, MRI, etc.). The corrected impulse responses are calculated by a known digital backpropagation algorithm, described in particular in the following articles:

"Ultrasonic beam steering through inhomogeneous layers with a time reversal mirror", C. DORME, M. FINK, *IEEE Transactions Ultrasonics, Ferroelectric and Frequency Control*, 43 (1), January 1996, pp. 167–175, "Focusing and steering through absorbing and aberrating layers: Application to ultrasonic propagation through the skull" Journal of Acoustical Society of America, 103 (5), May 1998, pp. 2403–2410, and "Propagation and backpropagation for ultrasonic wavefront design" Liu, D.-L., and Waag, R. C. *IEEE Trans. on Ultras. Ferro. and Freq. Contr.* 44(1):1–13 (1997).

In what follows, hri(t) will therefore denote the impulse responses for (real or virtual) elements lying against the aberrating layer. The virtual or real elements lying against the aberrating layer 3 will furthermore be referred to below as "focusing points" of index r between 1 and m.

When the transducers of the imaging array 5 emit acoustic signals $e_i(t)$, these signals generate acoustic signals fr(t) expressed as follows at the transducers r of the target array 6:

$$fr(t) = \sum_{i=1}^{n} hri(t) \otimes ei(t),$$

where $\hat{x}$ represents the time convolution operation.

After Fourier transform, this equation becomes:

$F(\omega k) = H(\omega k).E(\omega k)$, where:

$H(\omega k)$ is the transfer matrix, of size m*n, between the transducers Ti of the imaging array and the transducers Tr of the target array: the components $Hri(\omega k)$ of this matrix are the components of the Fourier transforms of the impulse responses $hri(t)$ at the frequency $\omega k$, $E(\omega k)$ is a vector whose components $E_i(\omega k)$ are the components of the Fourier transform of the aforementioned signals $e_i(t)$ at the frequency $\omega k$, and $F(\omega k)$ is a vector whose components $F_j(\omega k)$ are the components of the Fourier transform of the aforementioned signals $f_j(t)$ at the frequency $\omega k$.

By inverting each transfer matrix $H(\omega k)$, it is therefore possible to determine the vector $E(\omega k,j)$ which is suitable for generating, at the focusing point r corresponding to the transducer T'r of the target array, a vector $F(\omega k,j)$ all of whose components are as close as possible to the objective initially fixed (preferably all equal to zero, except for the component with index j corresponding to the transducer T'j, which is equal to 1 when the intention is to emit an acoustic pulse at the focusing point r), by virtue of the relationship:

$E(\omega k,j) = H^{-1}(\omega k).F(\omega k,j),$ where $H^{-1}(\omega k)$ is the inverse matrix of $H(\omega k)$.

$H^{-1}(\omega k)$ may be calculated by singular value decomposition, for example, which makes it possible to regularize the inversion of the matrix $H(\omega k)$.

Next, by inverse Fourier transform of the various components $Ei(\omega k,j)$ of the vector $E(\omega k,j)$, the various reference signals $ei(t,j)$ are determined which are suitable for focusing an acoustic pulse (or optionally another acoustic signal) at the focusing point r, when they are emitted by the various transducers Ti of the imaging array 5. Focusing of the imaging array 5 on each transducer of the target array 5 is therefore carried out by an inverse spatiotemporal filter.

The central unit CPU then follows a process of learning the aberrations at the target array due to the wall of the skull 3.

During this process, these aberrations are considered as a filter with a finite impulse response.

In the Fourier domain, this filter is defined at each frequency $\omega k$ by an amplitude $Gr(\omega k)$ and a phase $\phi_r(\omega k)$.

In order to calculate these coefficients, the phase and the amplitude of all the vectors Er are compared. To this end, the first stage is to eliminate the phase shifts introduced by the path differences between the imaging transducers Ti and the various focusing points indexed r. This is equivalent to selecting a particular focusing point r0 and introducing a linear phase shift for the others with the angular frequency: $\exp(-j\Delta\tau(ro,r,1)\omega)$ with $\Delta\tau(r0,r,i)=(d(r0,i)-d(r,i))/c$ where $d(r,i)$ is the distance between the transducer i and the focusing point r, and c is the average speed of the acoustic waves in the medium to be imaged, in this case the brain 2.

Once this correction has been carried out, the differences in amplitude and phase between the vectors Er are attributed to the aberrating layer 3 which lie against the target array.

The gain factor $Gj(\omega k)$ and the phase factor $\phi_j(\omega k)$ are then calculated for each focusing point r:

$$Gr(\omega_k) = \frac{\sqrt{\sum_{i=1}^{n} E_i(\omega_k, r0) \cdot E_i^*(\omega_k, r0)}}{\sqrt{\sum_{i=1}^{n} E_i(\omega_k, r) \cdot E_i^*(\omega_k, r)}}$$

$$\phi_r(\omega_k) = \frac{1}{n}\sum_{i=1}^{n}(\arg(E_i(\omega_k, r0)) - \arg(E_i(\omega_k, r)e^{-j\Delta\tau(t0,r,i)\omega_k}))$$

where Ei* is the complex conjugate value of Ei.

The pairs $\{Gj(\omega k), \phi_j(\omega k)\}$ correspond to the relative attenuation factor and relative phase shift introduced at each frequency by the portion of the aberrating layer 3 lying against the focusing point r. They therefore finally characterize the aberrations introduced by the aberrating layer portion lying against the target array.

The aberrations introduced by the aberrating layer 3 lying against the target transducers are then eliminated in all the p matrices $H(\omega k)=[Hji(\omega k)]$ defined above.

To this end, a new set of transfer matrices $H'(\omega k)=[H'ji(\omega k)]$ is calculated characterizing the propagation between the imaging array and the target array in a virtual medium for which only the aberrations lying against the imaging array remain:

$$H'_{ji}(\omega_k) = H_{ji}(\omega_k) \cdot \frac{1}{G_j(\omega_k)} e^{-j\phi_j(\omega_k)}.$$

For each transducer r of the target array, n components $E'i(\omega k,r)$ are then determined, i varying between 1 and n, such that $F(\omega k,r)=H'(\omega k).E'(\omega k,r)$, where $E'(\omega k,r)=[E'i(\omega k,r)]$ is a vector with n components, $F(\omega k,r)$ is a vector with m components $Fl(\omega k,r)$, l varying between 1 and m, these m components $Fl(\omega k,r)$ corresponding to a desired focusing of the acoustic waves at the frequency $\omega k$ on the focusing point r corresponding to a transducer of the target array.

For each focusing point r corresponding to a transducer of the target array, a vector of n reference time signals $e'(t,r)=[e'i(t,r)]$ is deduced therefrom, i varying between 1 and n, where $$e'_i(t, r) = \sum_{k=1}^{P} Ei(\omega k, r) \cdot e^{j\omega_k t}$$

in complex notation.

These reference signals $e'i(t,j)$ are adapted so that the emission of them respectively by the various transducers i of the imaging array generates an acoustic pulse focused on the transducer j of the target array in the absence of the aberrating layer lying against the target array.

It will be noted that, as a variant, the reference signals could be determined in the following way, after having determined the impulse responses $hri(t)$ and the p transfer matrices $H(\omega k)$:

the transfer matrices $H(\omega k)$ are corrected in order to overcome the aberrations generated by the aberrating wall 3 in the vicinity of each focusing point r, this correction being carried out on the basis of the impulse responses hri(t) determined previously, and corrected transfer matrices H'(ωk) are obtained in this way, by inverting the matrices H'(ωk), for each focusing point r corresponding to a transducer of the target array, n components E'i(ωk,r) are determined, i varying between 1 and n, such that F(ωk,r)=H'(ωk).E'(ωk,r), where E'(ωk,r)=[E'i(ωk,r)] is a vector with n components, F(ωk,r) is a vector with m components Fl(ωk,r), l varying between 1 and m, these m components Fl(ωk,r) corresponding to a desired focusing of the acoustic waves at the frequency ωk on the focusing point r corresponding to a transducer of the target array, and for each focusing point r corresponding to a transducer of the target array, a vector of n time signals e'(t,r)=[e'i(t,r)] is deduced therefrom, i varying between 1 and n, where $$e'_i(t, r) = \sum_{k=1}^{P} Ei(\omega k, r) \cdot e^{j\omega k, t}$$

in complex notation, the signals e'i(t,r) being said reference signals.

Advantageously, during the calculation of the matrices H'(ωk), the aberrating wall in the vicinity of each focusing point r corresponding to a transducer of the target array is assimilated to a filter, which has a finite impulse response and is defined at each frequency ωk by an amplitude Gr(ωk) and a phase $\phi_r(\omega k)$, which are calculated as follows:

$$G_r(\omega_k) = \frac{\sqrt{\sum_{i=1}^{n} H_{ri}(\omega_k) \cdot H_{ri}^*(\omega_k)}}{\sqrt{\sum_{i=1}^{n} H_{r0,i}(\omega_k) \cdot H_{r0,i}^*(\omega_k)}}$$

$$\phi_r(\omega_k) = \frac{1}{n} \sum_{i=1}^{n} (\arg(H_{ri}(\omega_k) e^{j\Delta\tau(i,r,r0)\omega_k}) - \arg(H_{r0,i}(\omega_k))), \text{ where:}$$

H*ri designates the complex conjugate value of Hri,
and Δτ(r0,r,i)=(d(r0,i)−d(r,i))/c, d(r,i) being the distance between the transducer i and the focusing point r, and d(r0,i) being the distance between the transducer i and a particular focusing point r0.

p corrected transfer matrices H'(ωk)=[H'ji(ωk)] are then calculated, where $$H'_{ji}(\omega_k) = H_{ji}(\omega_k) \cdot \frac{1}{G_j(\omega_k)} e^{-j\phi_j(\omega_k)},$$

which are used to determine the vectors E'i(ωk) as explained above, and therefore the various reference signals e'(t,r), r ranging from 1 to m.

The central unit CPU then learns to focus at a number R of predetermined focusing points lying in the brain 2, with indices q between m+1 and m+R, this substep consisting in determining for each of these focusing points q, moving step-by-step away from the transducers of the target array, reference signals e'i(t,q) to be emitted by the various transducers of the imaging array in order to generate a pulse focused on said focusing point q.

The reference signals e'i(t,q) are initially determined, for each new focusing point q, in the form e'i(t,q)=e'i(t+θi(q), q0) for each focusing point q, q0 being the index of a focusing point close to the focusing point q for which the reference signal has already been determined, the delay θi(q) initially being equal to a value δi(q)/c, where c is the average speed of the acoustic waves in the medium, and δi(q) is equal to a difference between, on the one hand, a distance between the transducer i of the imaging array and the focusing point q0, and, on the other hand, a distance between the transducer i of the imaging array and the focusing point q.

In the event that certain transducers with index v of the imaging array do not lie against the aberrating layer, it is furthermore desirable to correct the reference signals the corresponding signals e'v(t,q) by digital backpropagation from the virtual transducers (lying against the aberrating layer 3) to the real transducers (separated from said layer 3 by some gel 7 or the like), in a manner which is known per se, by the method which is the reverse of that described above in relation to the impulse responses.

The transducers of the imaging array are then made to emit, by iterations, the estimates obtained for the reference signals e'i(t,q), then signals $s_i$(t,q) back-scattered by the dissipative heterogeneous medium are picked up with the same transducers.

Next, these reference signals e'i(t,q) are modified for the next iteration in the following way:

$$e_i'(t) \rightarrow \alpha_i(q) \cdot e_i'(t - \tau_i(q))$$

where the values $\tau_i(q)$ and $\alpha_i(q)$ are a corrective delay and a corrective amplitude factor, which are calculated so as to maximize a coherence criterion C between said back-scattered signals.

Advantageously, this coherence criterion C may be the following:

$$C = \frac{<\left|\sum_{i=1}^{n} \alpha_i \cdot g_i(t - \tau_i, q)\right|^2>}{n \cdot \sum_{i=1}^{n} <\left|\alpha_i \cdot g_i(t - \tau_i, q)\right|^2>}, \text{ where:}$$

$g_i$(t,q)=$s_i$(t)$\hat{x}$e$_i$'(t,q) $\hat{x}$ representing the convolution operation, and <> represents a time average.

In this optimization process, the values $\tau_i$(q) may be calculated at each iteration so as to maximize a cross-correlation function, for transducers close to the imaging array, of the aforementioned signals $g_i$(t,q) and $g_{i+1}$(t,q), and the values $\alpha_i$(q) may be calculated so as to equalize the maximum amplitude of the functions $g_i$(t,q) on the index i.

The reference signals e'i(t,q), i ranging from 1 to n, are hence optimized so that they produce an acoustic signal focused precisely on the focusing point q lying in the brain. This optimization process has already been explained in more detail by Mallart et al. (The Van Cittert-Zernike theorem in pulse echo measurements, J. Acoust. Soc. Am. 90(5), November 1991, pp. 2716–2727; Adaptive focusing in scattering media through sound speed inhomogeneities: the Van Cittert Zernike approach and focusing criterion, J. Acoust. Soc. Am. 96(6), December 1994, pp. 3721–3732).

When this optimization is completed for a focusing point q, for example after 2 or 3 iterations when the criterion C has reached a predetermined value (in particular close to ⅔), operation proceeds to the next focusing point q+1, etc.

The reference signals e'i(t,q) obtained in this way are stored, for example in the memories M1–Mn.

Once the learning step is completed, it is in particular possible to produce echographic images of the brain 2, optionally at a fast rate which may be as high as the speed of a standard echograph, for example 20 to 30 images per second. In order to produce each of these images, the following procedure is adopted for each focusing point q belonging to the field to be observed:

the transducers Ti of the imaging array are respectively made to emit said reference signals ei(t,q), then said transducers of the imaging array are made to pick up signals si(t) back-scattered by the viscoelastic medium, the reference signal ei(t,q) emitted by each transducer of the imaging array is convoluted with the back-scattered signal si(t) picked up by this transducer, then the convolution products obtained in this way are summed.

It will be noted that the various aforementioned operations carried out during the learning step or the imaging step may either be programmed in the central unit CPU, or all or some of them may be performed by specialized circuits.

Furthermore, it will also be noted that all the transducers Ti, T'r could be used to produce the echographic images of the brain. In this case, the imaging array would be the same as the target array, and each of these two arrays would comprise all the transducers, the operation described above then being applied mutatis mutandis.

The invention claimed is:

1. A noninvasive method for focusing acoustic waves in a dissipative heterogeneous medium (2, 3) comprising a substantially homogeneous medium (2) surrounded at least partially by a dissipative aberrating layer (3) which generates aberrations in the propagation of the acoustic waves, the acoustic waves being emitted from outside the aberrating layer (3) and focused in the substantially homogeneous medium (2), characterized in that it includes the following steps:
  (a) an initial positioning step during which a number t greater than 2 of acoustic transducers (T1–Tn, T'1–T'm) are fixed in predetermined positions outside the aberrating layer (3), these transducers being in contact with said aberrating layer and forming at least:
    an imaging array (T1–Tn) which combines a number n between 1 and t of said transducers,
    and a target array (T'1–T'm) which combines a number m between 1 and t of said transducers,
  (b) a learning step itself comprising the following substeps:
    (b1) a substep of learning to focus the imaging array on the target array, during which substep:
    (b11) impulse responses hri(t) of the dissipative heterogeneous medium are determined, respectively between each transducer i of the imaging array and a plurality of focusing points r lying on the aberrating layer (3) in respective correspondence with transducers of the target array, these impulse responses being stored in digital form with a certain time sampling which determines a number p of frequency components of the impulse response, with respective frequencies ωk, i being an index between 1 and n which designates a transducer of the imaging array, r being an index between 1 and m which designates a focusing point corresponding to a transducer of the target array and k being an index between 1 and p which designates a frequency component,
    (b12) on the basis of these impulse responses, for each focusing point r corresponding to a transducer of the imaging array, a set of n reference time signals e'i(t,r) is calculated, i varying between 1 and n, such that if the aberrating wall were removed in the vicinity of the focusing point r, the emission of these reference signals by the various transducers i of the imaging array would generate a predetermined signal focused on the focusing point r,
    (b2) a substep of focusing at a number R of predetermined focusing points lying in the substantially homogeneous medium, with indices q between m+1 and m+R, this substep consisting in determining for each of these focusing points q, moving step-by-step away from the focusing points 1 to m corresponding to the transducers of the target array, reference signals e'i(t,q) to be emitted by the various transducers i of the imaging array in order to generate a pulse focused on said focusing point q, the reference signals e'i(t,q) being determined for each focusing point q by proceeding as follows:
      (b21) a first estimate of e'i(t,q), for i ranging from 1 to n, is calculated on the basis of at least one reference signal e'i(t,q0), q0 being the index of at least one focusing point close to the focusing point q for which the reference signal has already been determined, this calculation being performed by using an average speed of the acoustic waves in the substantially homogeneous medium (2),
      (b22) the transducers of the imaging array are made to emit, by iterations, the estimates previously obtained of the reference signals e'i(t,q), then signals $s_i(t,q)$ back-scattered by the dissipative heterogeneous medium are picked up with the same transducers, then these reference signals e'i(t,q) are modified for the next iteration in the following way:

$$e_i'(t) \to \alpha_i(q).e_i'(t-\tau_i(q))$$

where the values $\alpha_i(q)$ and $\tau_i(q)$ are a corrective amplitude factor and a corrective delay, which are calculated so as to maximize a coherence criterion C between said back-scattered signals, said iterations being stopped when the criterion C reaches a predetermined threshold,
    (b3) the reference signals e'i(t,q) are stored, at least for q between m+1 and m+R,
  (c) and a focusing step during which, for at least one of said focusing points q, the transducers of the imaging array are made to emit said reference signals e'$_i$(t,q), i being an index between 1 and n designating a transducer of the imaging array.

2. The method as claimed in claim 1, in which during substep (b11), when at least certain transducers (T1–Tm, T'1–T'm) are in contact with an intermediate heterogeneous medium which is itself in contact with the aberrating layer, the impulse responses hri(t) are corrected by digital back-propagation in order to simulate transducers lying directly in contact with the aberrating layer.

3. The method as claimed in claim 1 or claim 2, in which substep (b12) itself includes the following substeps:
  (b121) p transfer matrices H(ωk)=[Hri(ωk)] are determined, i ranging from 1 to n and r ranging from 1 to m, where Hri(ωk) is the value, at the frequency ωk, of the Fourier transform of the impulse response hri(t), (b122) for each focusing point r corresponding to a transducer of the target array, n components Ei(ωk,r) are determined, i varying between 1 and n, such that F(ωk,r)=H(ωk).E(ωk,r), where E(ωk,r)=[Ei(ωk,r)] is a vector with n components, F(ωk,r) is a vector with m components Fl(ωk,r), l varying between 1 and m, these m components Fl(ωk,r) corresponding to a desired focusing of the acoustic waves at the frequency ωk on the focusing point r corresponding to a transducer of the target array, (b123) for each focusing point r corresponding to a transducer of the target array, a vector of n time signals e(t,r)=[ei(t,r)] is deduced therefrom, i varying between 1 and n, where $$e'_i(t, r) = \sum_{k=1}^{P} Ei(\omega k, r) \cdot e^{j\omega k, t}$$

in complex notation, these signals ei(t,r) being adapted so that the emission of them respectively by the various transducers i of the imaging array generates an acoustic pulse focused on the focusing point r of the target array, (b124) a substep of correcting the aberrations generated by the aberrating layer between the substantially homogeneous medium and each target transducer r, these aberrations being estimated on the basis of the measurements carried out previously, the aberrations estimated in this way being used to calculate said reference time signals e'i(t,r).

4. The method as claimed in claim 3, in which p matrices $H^{-1}(\omega k)$ are calculated during substep (b122), respectively by regularization and inversion of the transfer matrices H(ωk), and the vector E(ωk,r) is calculated for each transducer r of the target array by the formula:

$$E(\omega k, r) = H^{-1}(\omega k).F(\omega k, j).$$

5. The method as claimed in claim 3 or claim 4, in which during step (b122), the components Fl(ωk,r) of the vector F(ωk,r) corresponding to the spatial distribution of the desired field at the frequency ωk are equal to 0 for l≠r and to 1 for l=r.

6. The method as claimed in any one of claims 3 to 5, in which during substep (b124), the aberrating wall in the vicinity of each focusing point r corresponding to a transducer of the target array is assimilated to a filter, which has a finite impulse response and is defined at each frequency ωk by an amplitude Gr(ωk) and a phase φ$_r$(ωk), substep (b124) itself including the following substeps:

(b1241) for each frequency ok, the amplitude Gr(ωk) and the phase φ$_r$(ωk) are calculated on the basis either of the signals ei(t,r) or of the vectors E(ωk,r), (b1242) p corrected transfer matrices H'(ωk)=[H'ji(ωk)] are calculated, where $$H'_{ji}(\omega_k) = H_{ji}(\omega_k) \cdot \frac{1}{G_j(\omega_k)} e^{-j\phi_j(\omega_k)},$$

(b1243) for each transducer r of the target array, n components E'i(ωk,r) are determined, i varying between 1 and n, such that F(ωk,r)=H'(ωk).E'(ωk,r), where E'(ωk,r)=[E'i(ωk,r)] is a vector with n components, F(ωk,r) is a vector with m components Fl(ωk,r), l varying between 1 and m, these m components Fl(ωk,r) corresponding to a desired focusing of the acoustic waves at the frequency ωk on the focusing point r corresponding to a transducer of the target array, (b1244) for each focusing point r corresponding to a transducer of the target array, a vector of n reference time signals e'(t,r)=[e'i(t,r)] is deduced therefrom, i varying between 1 and n, where $$e'_i(t, r) = \sum_{k=1}^{P} Ei(\omega k, r) \cdot e^{j\omega k, t}$$

in complex notation.

7. The method as claimed in claim 6, in which during substep (b1241), the amplitude Gr(ωk) and the phase φ$_r$(ωk) are calculated as follows:

$$Gr(\omega_k) = \frac{\sqrt{\sum_{i=1}^{n} E_i(\omega_k, r0) \cdot E_i^*(\omega_k, r0)}}{\sqrt{\sum_{i=1}^{n} E_i(\omega_k, r) \cdot E_i^*(\omega_k, r)}}$$

$$\phi_r(\omega_k) = \frac{1}{n}\sum_{i=1}^{n}(\arg(E_i(\omega_k, r0)) - \arg(E_i(\omega_k, r)e^{-j\Delta\tau(r0,r,i)\omega_k}))$$

where:

Ei* is the complex conjugate value of Ei, and Δτ(r0,r,i)=(d(r0,i)−d(r,i))/c, d(r,i) being the distance between the transducer i and the focusing point r, and d(r0,i) being the distance between the transducer i and a particular focusing point r0.

8. The method as claimed in claim 1 or claim 2, in which substep (b12) itself includes the following substeps:

(b121) p transfer matrices H(ωk)=[Hri(ωk)] are determined, i ranging from 1 to n and r ranging from 1 to m, where Hri(ωk) is the value, at the frequency ωk, of the Fourier transform of the impulse response hri(t), (b122') the transfer matrices H(ωk) are corrected in order to overcome the aberrations generated by the aberrating wall in the vicinity of each focusing point r, this correction being carried out on the basis of the impulse responses hri(t) determined previously, and corrected transfer matrices H'(ωk) are obtained in this way, (b123') for each focusing point r corresponding to a transducer of the target array, n components E'i(ωk,r) are determined, i varying between 1 and n, such that F(ωk,r)=H'(ωk).E'(ωk,r), where E'(ωk,r)=[E'i(ωk,r)] is a vector with n components, F(ωk,r) is a vector with m components Fl(ωk,r), l varying between 1 and m, these m components Fl(ωk,r) corresponding to a desired focusing of the acoustic waves at the frequency ωk on the focusing point r corresponding to a transducer of the target array, (b124') for each focusing point r corresponding to a transducer of the target array, a vector of n time signals e'(t,r)=[e'i(t,r)] is deduced therefrom, i varying between 1 and n, where $$e'_i(t, r) = \sum_{k=1}^{P} E'i(\omega k, r) \cdot e^{j\omega k, t}$$

in complex notation, the signals e'i(t,r) being said reference signals.

9. The method as claimed in claim 8, in which p matrices $H'^{-1}(\omega k)$ are calculated during substep (b123'), respectively by regularization and inversion of the transfer matrices $H'(\omega k)$, and the vector $E'(\omega k,r)$ is calculated for each transducer r of the target array by the formula:

$$E'(\omega k,r)=H'^{-1}(\omega k).F(\omega k,j).$$

10. The method as claimed in claim 8 or claim 9, in which during step (b123'), the components Fl($\omega$k,r) of the vector F($\omega$k,r) corresponding to the spatial distribution of the desired field at the frequency $\omega$k are equal to 0 for l≠r and to 1 for l=r.

11. The method as claimed in any one of claims 8 to 10, in which during substep (b122'), the aberrating wall in the vicinity of each focusing point r corresponding to a transducer of the target array is assimilated to a filter, which has a finite impulse response and is defined at each frequency $\omega$k by an amplitude Gr($\omega$k) and a phase $\phi_r$($\omega$k), substep (b122') itself including the following substeps:
(b122'1) for each frequency $\omega$k, the amplitude Gr($\omega$k) and the phase $\phi_r$($\omega$k) are calculated on the basis of the impulse responses determined previously,
(b122'2) p corrected transfer matrices H'($\omega$k)=[H'ji($\omega$k)] are calculated, where $$H'_{ji}(\omega_k) = H_{ji}(\omega_k) \cdot \frac{1}{G_j(\omega_k)} e^{-j\phi_j(\omega_k)}.$$

12. The method as claimed in claim 11, in which during substep (b122'1), the amplitude Gr($\omega$k) and the phase $\phi_r$($\omega$k) are calculated for each frequency $\omega$k in the following way:

$$G_r(\omega_k) = \frac{\sqrt{\sum_{i=1}^{n} H_{ri}(\omega_k) \cdot H_{ri}^*(\omega_k)}}{\sqrt{\sum_{i=1}^{n} H_{r0,i}(\omega_k) \cdot H_{r0,i}^*(\omega_k)}}$$

$$\phi_r(\omega_k) = \frac{1}{n}\sum_{i=1}^{n} (\arg(H_{ri}(\omega_k)e^{j\Delta\tau(i,r,r0)\omega_k}) - \arg(H_{r0,i}(\omega_k))), \text{ where:}$$

H*ri designates the complex conjugate value of Hri,
and $\Delta\tau(r0,r,i)=(d(r0,i)-d(r,i))/c$, d(r,i) being the distance between the transducer i and the focusing point r, and d(r0,i) being the distance between the transducer i and a particular focusing point r0.

13. The method as claimed in any one of the preceding claims, in which during step (c), substep (c1) is followed by the following substeps:
(c2) said transducers of the imaging array are made to pick up signals $s_i$(t) back-scattered by the dissipative heterogeneous medium,
(c3) the reference signal emitted by each transducer of the imaging array is convoluted with the back-scattered signal picked up by this transducer,
(c4) then the convolution products obtained in this way are summed,
step (c) being repeated for a plurality of points lying in the substantially homogeneous medium.

14. The method as claimed in any one of the preceding claims, in which during substep (b21), the first estimate of each reference signal is e'i(t,q)=e'i(ts+θi(q),q0) for each focusing point q, q0 being the index of a focusing point close to the focusing point q for which the reference signal has already been determined, θi(q) being a delay equal to a value δi(q)/c, where c is the average speed of the acoustic waves in the medium, and δi(q) is equal to a difference between, on the one hand, a distance between the transducer i of the imaging array and the focusing point q0, and, on the other hand, a distance between the transducer i of the imaging array and the focusing point q.

15. The method as claimed in any one of the preceding claims, in which during substep (b2), when at least certain transducers with index v of the imaging array are not directly in contact with the aberrating layer, the corresponding signals e'$_v$(t,q) are corrected by digital backpropagation in order to simulate transducers placed in direct contact with the aberrating layer.

16. The method as claimed in any one of the preceding claims, in which during substep (b22), the values $\alpha_i$(q) and $\tau_i$(q) are looked for to maximize the following coherence criterion C:

$$C = \frac{<\left|\sum_{i=1}^{n} \alpha_i \cdot g_i(t-\tau_i q)\right|^2>}{n \cdot \sum_{i=1}^{n} <|\alpha_i \cdot g_i(t-\tau_i, q)|^2>}, \text{ where:}$$

$g_i$(t,q)=$s_i$(t)$\hat{x}$e'$_i$(t,q), $\hat{x}$ representing the convolution operation,
and <> represents a time average.

17. The method as claimed in claim 16, in which during substep (b22), the values $\tau_i$(q) are calculated by maximizing a cross-correlation function, for transducers close to the imaging array, of the signals $g_i$(t,q) and $g_{i+1}$(t,q).

18. The method as claimed in claim 16 or claim 17, in which during substep (b22), the values $\alpha_i$(q) are calculated so as to equalize the maximum amplitude of the functions $g_i$(t,q) on the index i.

19. The method as claimed in any one of the preceding claims, in which substep (b22) relating to each focusing point q is carried out immediately after substep (b21) relating to the same focusing point q.

20. The method as claimed in any one of the preceding claims, in which the dissipative heterogeneous medium consists of the brain surrounded by the skull.

21. The method as claimed in any one of the preceding claims, in which:
either the imaging array and the target array are two separate arrays arranged on either side of the dissipative heterogeneous medium,
or all the transducers belong both to the imaging array and to the target array.

22. The method as claimed in any one of the preceding claims, in which the acoustic waves are ultrasound waves.

23. A device (1) designed for carrying out a method as claimed in any one of the preceding claims, this device including a number t greater than 2 of acoustic transducers (T1–Tn, T'1–T'm) intended to be fixed in predetermined positions outside the aberrating layer (3), these transducers being controlled by at least one central electronic unit (CPU) and forming at least:
an imaging array (T1–Tn) which combines a number n between 1 and t of said transducers, and a target array (T'1–T'm) which combines a number m between 1 and t of said transducers, the central electronic unit being designed to follow the following steps:
- (b) a learning step itself comprising the following substeps:
- (b1) a substep of learning to focus the imaging array on the target array, during which substep:
- (b11) impulse responses hri(t) of the dissipative heterogeneous medium are determined, respectively between each transducer i of the imaging array and a plurality of focusing points r lying on the aberrating layer in respective correspondence with transducers of the target array, these impulse responses being stored in digital form with a certain time sampling which determines a number p of frequency components of the impulse response, with respective frequencies $\omega k$, i being an index between 1 and n which designates a transducer of the imaging array, r being an index between 1 and m which designates a focusing point corresponding to a transducer of the target array and k being an index between 1 and p which designates a frequency component,
- (b12) on the basis of these impulse responses, for each focusing point r corresponding to a transducer of the imaging array, a set of n reference time signals e'i(t,r) is calculated, i varying between 1 and n, such that if the aberrating wall were removed in the vicinity of the focusing point r, the emission of these reference signals by the various transducers i of the imaging array would generate an acoustic pulse focused on the focusing point r,
- (b2) a substep of focusing at a number R of predetermined focusing points lying in the substantially homogeneous medium, with indices q between m+1 and m+R, this substep consisting in determining for each of these focusing points q, moving step-by-step away from the focusing points 1 to m corresponding to the transducers of the target array, reference signals e'i(t,q) to be emitted by the various transducers i of the imaging array in order to generate a predetermined signal focused on said focusing point q, the reference signals e'i(t,q) being determined for each focusing point q by proceeding as follows:
- (b21) a first estimate of e'i(t,q), for i ranging from 1 to 4, is calculated on the basis of at least one reference signal e'i(t,q0), q0 being the index of at least one focusing point close to the focusing point q for which the reference signal has already been determined, this calculation being performed by using an average speed of the acoustic waves in the substantially homogeneous medium (2),
- (b22) the transducers of the imaging array are made to emit, by iterations, the estimates previously obtained of the reference signals e'i(t,q), then signals $s_i(t,q)$ back-scattered by the dissipative heterogeneous medium are picked up with the same transducers, then these reference signals e'i(t,q) are modified for the next iteration in the following way:

$$e_i'(t) \rightarrow \alpha_i(q).e_i'(t-\tau_i(q))$$

where the values $\alpha_i(q)$ and $\tau_i(q)$ are a corrective amplitude factor and a corrective delay, which are calculated so as to maximize a coherence criterion C between said back-scattered signals, said iterations being stopped when the criterion C reaches a predetermined threshold,
- (b3) the reference signals e'i(t,q) are stored, at least for q between m+1 and m+R,
- (c) and a focusing step during which, for at least one of said focusing points q, the transducers of the imaging array are made to emit said reference signals e'i(t,q), i being an index between 1 and n designating a transducer of the imaging array.

* * * * *

UNITED STATES PATENT AND TRADEMARK OFFICE
CERTIFICATE OF CORRECTION

| | | |
|---|---|---|
| PATENT NO. | : 7,101,337 B2 | Page 1 of 1 |
| APPLICATION NO. | : 10/399634 | |
| DATED | : September 5, 2006 | |
| INVENTOR(S) | : Aubry et al. | |

It is certified that error appears in the above-identified patent and that said Letters Patent is hereby corrected as shown below:

<u>In the Title Page</u>:
At Section (75), please delete "Jean-Francois" and insert -- Jean-François --
At Section (73), please delete "Rechercher" and insert -- Recherche --
At Section (57), please delete the entire abstract and insert -- A noninvasive method for focusing acoustic waves in a dissipative heterogeneous medium is disclosed. A substantially homogenous medium may be surrounded at least partially by a dissipative aberrating layer which generates aberrations in the propagation of the acoustic waves. The acoustic waves may be admitted from outside the aberrating layer and focused in the substantially homogenous medium.--

Signed and Sealed this

Fifteenth Day of May, 2007

JON W. DUDAS
*Director of the United States Patent and Trademark Office*